United States Patent [19]

O'Neill et al.

[11] Patent Number: 5,543,055
[45] Date of Patent: Aug. 6, 1996

[54] PURIFICATIONS OF FLOURINATED DIMETHYL ETHERS

[75] Inventors: Gerald J. O'Neill, Arlington, Mass.; Robert J. Bulka, Merrimack, N.H.

[73] Assignee: Hampshire Chemical Corp., Lexington, Mass.

[21] Appl. No.: 466,096

[22] Filed: Jun. 6, 1995

[51] Int. Cl.$^6$ .................................................. B01D 15/00
[52] U.S. Cl. ........................ 210/638; 210/661; 210/690
[58] Field of Search .................................. 568/683, 684; 210/638, 661, 664, 690

[56] References Cited

U.S. PATENT DOCUMENTS

| | | | |
|---|---|---|---|
| 2,066,905 | 1/1937 | Booth | 260/151 |
| 2,533,132 | 12/1950 | McBee | 260/653 |
| 3,461,213 | 8/1969 | Terrell | 568/684 |
| 3,663,715 | 5/1972 | Terrell | 568/684 |
| 3,689,459 | 9/1972 | Reagan | 260/614 F |
| 3,806,602 | 4/1974 | Croix | 424/342 |
| 3,862,241 | 1/1975 | Terrell | 260/614 |
| 3,879,474 | 4/1975 | Croix | 260/614 F |
| 3,887,439 | 6/1975 | Hutchinson | 203/63 |
| 3,897,502 | 7/1975 | Russell et al. | 260/614 F |
| 4,025,567 | 5/1977 | Hutchinson et al. | 260/616 |
| 4,041,148 | 8/1977 | Simons et al. | 424/45 |
| 4,113,435 | 9/1978 | Lagow et al. | 422/191 |
| 4,139,607 | 2/1979 | Simons et al. | 424/45 |
| 4,149,018 | 4/1979 | Bell et al. | 568/684 |
| 4,172,016 | 10/1979 | Abe et al. | 204/59 F |
| 4,504,686 | 9/1985 | Takamatsu | 568/684 |
| 4,874,901 | 10/1989 | Halpern et al. | 568/683 |
| 4,961,321 | 10/1990 | O'Neill et al. | 62/114 |
| 5,026,924 | 6/1991 | Cicco | 568/683 |
| 5,084,146 | 1/1992 | Huang | 204/59 F |
| 5,185,474 | 2/1993 | O'Neill | 568/684 |
| 5,196,600 | 3/1993 | O'Neill | 568/684 |
| 5,278,342 | 1/1994 | O'Neill | 568/684 |

FOREIGN PATENT DOCUMENTS

| | | |
|---|---|---|
| 949978 | 6/1974 | Canada . |
| 0005810 | 12/1979 | European Pat. Off. . |
| 0352034 | 1/1990 | European Pat. Off. . |
| 0450855 | 10/1991 | European Pat. Off. . |
| 0518506 | 12/1992 | European Pat. Off. . |
| 2248617 | 4/1992 | United Kingdom . |

OTHER PUBLICATIONS

Chemical Abstract, vol. 52,44676 (1958);"Methylene Derivatives as Intermediates in Polar Reactions", Journal of the American Chem. Society, 79, 5493–6 (1957).
Chemical Abstract, vol. 55,12270 (1961).
Chemical Abstract, vol. 55,23312 (b) (1961).
Chemical Abstract, vol. 55,27012 (i) (1961).
Chemical Abstract, vol. 56,9938 (c) (1962).
Chemical Abstract, vol. 82,43287 (j) (1975).
Chemical Abstract, vol. 73,10480 (1970).
Chemical Abstract, vol. 58,23556 (g) (1964).
Chemical Abstract, vol. 53,27013 (a) (1961).
Chemical Abstract, vol. 74,2292 (1952).
Chemical Abstract, vol. 76,1387 (1954).

*Primary Examiner*—Frank Spear
*Attorney, Agent, or Firm*—Nields & Lemack

[57] ABSTRACT

A process for the purification of bis(difluoromethyl)ether. Bis(difluoromethyl)ether is exposed to molecular sieves in order to reduce or completely remove impurities. In a further embodiment, the present invention optionally includes means for preferentially inhibiting the formation of $CF_2HOCCl_3$ in the formation of bis(difluoromethyl)ether prior to exposing the bis(difluoromethyl)ether to the molecular sieves.

8 Claims, No Drawings

PURIFICATIONS OF FLOURINATED DIMETHYL ETHERS

BACKGROUND OF THE INVENTION

This invention relates in general to fluorinated dimethyl ethers, and specifically to bis(difluoromethyl)ether ($CHF_2OCHF_2$), which have utility has CFC alternatives, particulary for use as refrigerants, blowing agents, etc.

Bis(difhoromethyl)ether has been prepared previously by chlorination of dimethyl ether followed by isolation and fluorination of bis(dichloromethyl)ether. The chlorination step resulted in a complex mixture of chlorinated dimethyl ethers, some of which were unstable, e.g. to distillation, from which bis(dichloromethyl)ether was separated. Moreover, chloromethyl methyl ether and bis(chloromethyl)ether are produced by this reaction, and are carcinogens.

Another approach to the synthesis of methyl difluoromethyl ether is disclosed by Hine and Porter in *Methylene derivatives as intermediates in polar reaction VIII. Difluoromethylene in the Reaction of Chlorodifluoromethane with Sodium Methoxide*, published in the Journal of the American Chemical Society 79, 5493–6 (1957). This article describes a reaction mechanism wherein the desired difluoromethyl-methyl-ether is synthesized in a batch reaction in a fixed ratio with the by-product trimethyl-orthoformate, while continuously refluxing the unreacted feed. However, not only does this reaction produce large amounts of trimethylorthoformate, but also the product itself breaks down to trimethylorthoformate, resulting in less than advantageous yields of the desired difluoromethyl methyl ether.

U.S. Pat. No. 5,185,474, the disclosure of which is hereby incorporated by reference, discloses avoiding the production of such carcinogens and unstable compounds by using methyl difluoromethyl ether as a starting material. The methyl difluoromethyl ether is chlorinated to produce a reaction mixture including at least one compound of the formula $CF_2HOCH_{3-z}Cl_z$, wherein z is 1, 2, or 3. The mixture can then be fluorinated, or any one of the chlorination compounds first separated from the mixture and separately fluorinated.

However, unreacted starting material (difluoromethyl methyl ether) and a by-product (chlorofluoromethane) formed in the preparation of bis(difluoromethyl)ether, remain as impurities in the product after distillation. They cannot be completely removed during distillation in view of the proximity of their boiling points to that of bis(difluoromethyl)ether, or possibly in view of the unconfirmed formation of an azeotrope. The presence of these impurities in bis(difluoromethyl)ether can deleteriously effect its performance as a refrigerant, for example. Moreover, chorofluoro-methane is a known carcinogen.

Accordingly, it is therefore an object of the present invention to provide purified bis(difluoromethyl)ether.

It is an further object of the present invention to provide a process for the production of purified bis(difluoromethyl) ether.

SUMMARY OF THE INVENTION

The problems of the prior art have been overcome by the present invention, which provides a process for the purification of bis(difluoromethyl)ether. More specifically, the process of the present invention includes exposing bis(difluoromethyl)ether to molecular sieves in order to seduce or completely remove impurities. Molecular sieves or zeolites have been used for the separation or purification of both gaseous and liquid feedstocks. Whether a molecule will be adsorbed by a particular size of molecular sieve is not predictable. Adsorption depends not only on size and shape of the apertures in the sieve crystal relative to the size and shape of the molecule, but also on other properties such as the polarity of the molecule to be adsorbed, the existence of a permanent dipole moment, the sieve cation distribution and charge and the effect of its electric field on the molecule to be adsorbed. The inventors of the present invention have discovered that certain size molecular sieves are very effective in removing impurities from bis(difluoromethyl)ether.

In a further embodiment, the present invention optionally includes means for preferentially inhibiting the formation of $CF_2HOCCl_3$ in the formation of bis(difluoromethyl)ether prior to exposing the bis(difluoromethyl)ether to the molecular sieves.

DETAILED DESCRIPTION OF THE INVENTION

The methyl difluoromethyl ether which is regarded as the starting material for producing bis(difluoromethyl)ether is a known compound which may be prepared in the manner reported by Hine and Porter in their aforementioned article published in the *Journal of the American Chemical Society*. Specifically, difluoromethyl methyl ether can be produced by reaction of sodium methoxide (NaOMe) with chlorodifluoromethane ($CF_2HCl$), which reaction may be represented as follows:

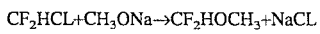

$CF_2HCL + CH_3ONa \rightarrow CF_2HOCH_3 + NaCL$

Briefly, the method involves forming an alcohol solution of sodium methoxide and bubbling the chlorodifluoromethane slowly into the reaction mixture to obtain the methyldifluoromethyl ether as a residue in the reaction mixture. Some product is entrained with unreacted $CF_2HCl$ and can be separated from it in a distillation operation.

The starting ether, $CHF_2OCH_3$, also might be prepared by first reacting NaOH with $CH_3OH$, in effect making $CH_3ONa$, and then reacting it with $CF_2HCl$. However, water is also formed in the $NaOH/CH_3OH$ reaction. The effect water has on the subsequent reaction to form $CHF_2OCH_3$ is to reduce the yield of $CHF_2OCH_3$.

The chlorination and fluorination steps used to produce bis(difluoromethyl)ether can be represented as follows:

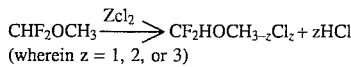

$CHF_2OCH_3 \xrightarrow{ZCl_2} CF_2HOCH_{3-z}Cl_z + zHCl$
(wherein z = 1, 2, or 3)

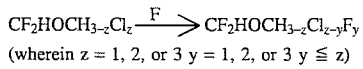

$CF_2HOCH_{3-z}Cl_z \xrightarrow{F} CF_2HOCH_{3-z}Cl_{z-y}F_y$
(wherein z = 1, 2, or 3 y = 1, 2, or 3 y ≦ z)

The formation of $CF_2HOCH_{3-z}Cl_z$ wherein z=3 in the above reaction scheme can be inhibited or even eliminated upon the addition of an oxygen source, preferably air, to the vapor phase reaction medium, in accordance with U.S. Pat. No. 5,278,342 the disclosure of which is hereby incorporated by reference. Rather than inhibiting the three chlorination products equally, the addition of oxygen surprisingly preferentially inhibits the formation of $CF_2HOCCl_3$. Any oxygen source not deleterious to the production of the desired compounds could be used, including oxygen-containing compounds which liberate oxygen in situ. The oxygen should be present in an amount effective for the desired inhibition. In the case of air, preferably the air is added in an amount from about 1.5 to about 5.5% of the total gas flow. Those skilled in the art will recognize that where pure oxygen is used, the amounts will be about ⅕ that of air. Preferably the oxygen source is added to the reaction medium for as long as the chlorine gas is flowing.

It has been found that $CHF_2OCH_3$ may be suitably chlorinated by liquefying the $CHF_2OCH_3$ and reacting it with chlorine gas while irradiating with a source of visible light. Alternatively, one may use other light sources such as ultraviolet light or heat, a catalyst or a free radical initiator to aid in the reaction. The chlorination products of $CHF_2OCH_3$ can be readily separated prior to fluorination or the reaction mixture can be fluorinated without separation to give an admixture of $CF_2HOCCl_2F$, $CF_2HOCF_2Cl$, $CF_2HOCH_2F$, $CF_2HOCFHCl$, $CF_2HOCF_2H$. All separations may be effected by fractional distillation.

A preferred method of chlorinating the $CHF_2OCH_3$ is to maintain the $CHF_2OCH_3$ in a vapor phase and react it with chlorine gas while subjecting the chlorination reaction to a source of light, preferably visible or ultraviolet light. Alternatively, other reaction aids such as a catalyst, heat or a free radical initiator may be used instead of light in the chlorination reaction.

In the preferred fluorination procedure, the chlorinated reaction product is reacted with anhydrous hydrogen fluoride (HF), which reaction may be represented as follows:

$$2CF_2HOCCl_3+3HF \rightarrow CF_2HOCFCl_2+CF_2HOCF_2Cl+3HCl$$

Alternatively, the HF may be diluted with an organic solvent, preferably a dipolar aprotic solvent such as methyl pyrrolidone, in order to reduce fragmentation of the fluorinated material, resulting in higher yields of desired product with less by-product generation. Other sources of fluorine for the fluorination step include metal fluorides that can form salts of the $HF_2^\ominus$ anion, such as $KHF_2$, $NaHF_2$, $LiHF_2$, $NH_4HF_2$, etc., and pyridine salts of HF and NaF and KF in suitable solvents.

The resultant fluorinated products may be separated by distillation or by the process as taught in U.S. Pat. Nos. 4,025,567 or 3,887,439, the disclosures of which are incorporated herein by reference.

In order to purify the resulting product (either prior to or after distillation), molecular sieves that have been preheated to about 200°–400° C., preferably to about 240°–250° C. are used. Heating times are not critical, and can range from about 3 hours to about 20 hours. Preferably the sieves are pumped under a vacuum while still warm. If vacuum treating is not used, the molecular sieves should be heated to temperatures at the higher end of the 200°–400° C. range. Suitable sieve sizes include 3, 4, 5 and 10 Å for removing difluoromethyl methyl ether. Removal of chlorofluoromethane is more selective; sieve sizes less than 4 Å were not effective. Preferably sieve sizes of 4 or 5 Å are used to remove chlorofluoromethane, most preferably 4 Å.

The molecular sieves can be contacted with the impure bis(difluoromethyl)ether either in a continuous process, i.e., under constant flow, or in a static system. In the continuous process, the weight ratio of bis(difluoromethyl)ether to molecular sieves can range from about 0.04 to about 0.6, preferably 0.07 to 0.33. In the static system, the weight of bis(difluoromethyl)ether should exceed that of the sieves. A suitable ratio is from about 1 to about 7, preferably from 1.8 to 4.8 .

The molecular sieves can be contacted with bis(difluoromethyl)ether at ambient temperature. Higher temperatures (ex., up to 100° C.) are operative and can increase the rate at which equilibrium is established between adsorption and desorption, but the amount of material adsorbed decreases with increases in temperature. Unless adsorption is very high and there is some advantage to be gained by rapid establishment of equilibrium, a higher temperature should not normally be used. Lower temperatures (ex., 0°–20 C.) are also operative; there can be an advantage to the use of sub-ambient temperatures in view of higher adsorption. Preferred temperatures are from about 20°–35° C., more preferably about 25° C.

A suitable contact time in the continuous process is from about 2 to about 6 minutes. Suitable contact time in the static system is about 3 hours, but can be as high as 15 hours.

The present invention will now be further illustrated by the following examples.

EXAMPLE 1 a) Preparation of $CF_2HOCH_3$

A 25 wt % solution of sodium methoxide in methanol (1533.1 g) containing 7.1 moles of sodium methoxide was placed in a 4 liter jacketed autoclave fitted with a temperature sensor, a pressure gauge and a dipleg. The vessel was cooled to 0°–5° C. and chlorodifluoromethane (318.2 g, 3.70 moles) added over a period of 2.5 hours with agitation. When the addition of gas had been completed, the autoclave was slowly warmed to about 60° C. while venting gaseous products through the water-cooled condenser into a collection trap cooled to about −70° C.

When all volatile material had been collected unreacted $CHF_2Cl$ was removed at −20° C. and the remaining $CF_2HOCH_3$ transferred to a metal cylinder. The recovered difluoromethyl methyl ether (150.0 g, 1.83 moles) represented a yield of 49.4% based on $CF_2HCl$.

b) Chlorination of $CF_2HOCH_3$

Chlorine and $CF_2HOCH_3$ in a gaseous phase are passed through separate condensers cooled to 0° C. and then the gas streams combine and pass into one arm of a U-shaped reactor, irradiated with visible light or UV. Both arms of the reactor are jacketed and cooled with water.

There is an outlet at the bottom of the U to which is attached a product collection flask. A Dewar-type condenser cooled to −50° C. is attached to the outlet of the second arm of the U-tube and, in turn, it is connected in series with a cold trap to collect unreacted chlorine and an NaOH scrubber to remove HCl. The reaction is normally carried out at atmospheric pressure, but higher or lower pressure can be used. Temperature should not be allowed to rise much above 50° C. in the reactor to avoid attack on the glass.

In practice, the apparatus is flushed with nitrogen and then chlorine and $CF_2HOCH_3$ are fed to the reactor at rates such that the ratio of the flow of chlorine to that of the ether is maintained at about 2.5:1 for optimum results, i.e., yield of $CF_2HOCHCl_2$. A predominant amount of any one of the three products can be obtained by changing the ratio of the gas flows.

After the passage of 2.3 moles of chlorine and 0.9 moles of $CHF_2OCH_3$, 136.6 g of product were recovered. GC analysis of the product mixture showed $CF_2HOCH_2Cl$ 10.0%, $CF_2HOCHCl_2$ 62.4%, and $CF_2HOCCl_3$ 22.2%.

c) Fluorination of $CHF_2OCHCl_1$ with HF

The chlorinated $CHF_2OCH_3$ (40.0 g) containing 46.1% $CF_2HOCHCl_2$ in a stainless steel cylinder was then cooled in ice before adding anhydrous HF (30.0 g). The cylinder was closed with a valve and pressure gauge and then was placed in a water bath at 60° C. for 3 hours. The cylinder was then vented through a NaOH scrubber and volatile products collected in a trap cooled at −70° C. The weight of product recovered from the trap was 16.8 g. It contained 71.8% $CF_2HOCF_2H$ by GC analysis, corresponding to a yield of 83.8% of $CF_2HOCF_2H$.

When conducted on a larger scale (e.g., 5 gallons), almost quantitative yields of $CF_2HOCF_2H$ (based on $CF_2HOCHCl_2$) were obtained.

EXAMPLE 2

The chlorination apparatus consisted of two vertical lengths of jacketed glass tubing, 4 feet long by 2 inches I.D., connected at the lower ends in a U-tube fashion by a short length of unjacketed 2 inch I.D. tubing. A drain tube led from the lowest point of the U-tube arrangement so that product could be collected as it formed and removed continuously from the apparatus or alternatively allowed to accumulate in a receiver. Three 150 watt incandescent flood lamps were arranged along the length of each tube.

The gases were fed into the upper end of one arm of the U-tube arrangement. Flow rates were measured by calibrated mass flowmeters. A low temperature condenser on the outlet of the second arm of the U-tube returned unreacted E-152a and chlorine to the illuminated reaction zone. Hydrogen chloride by-product and air passed through the condenser into a water scrubber where the hydrogen chloride was removed.

A mixture of methanol and water, cooled to 0° to 5° C. was circulated through the cooling jackets of the apparatus.

In a typical run, coolant at a temperature of 0° to 5° C. is circulated through the cooling jackets, the flood lamps were turned on and dry ice placed in the low temperature condenser. Chlorine was introduced into the apparatus first, followed by difluoromethyl ether and air in the desired ratios. Product was removed at intervals from the receiver and washed with saturated $NaHCO_3$ solution to remove HCl. Since the reaction was continuous, it could proceed for any length of time desired. At the end of the reaction, gas flows were stopped and product allowed to drain from the vertical reactor tubes into the receiver.

The results are tabulated in Table 1 below. Examples 6-29-1 to 6-29-7 show the distribution of products normally obtained without the addition of air to the gas stream. Examples 7-7-3 through 7-8-6 show the effect of the addition of air in diminishing amounts.

EXAMPLE 3

A sample of chlorinated difluoromethyl ether mixture (25 g) containing 50% $CF_2HOCCl_3$, was placed in a polyethylene flask fitted with an inlet tube for nitrogen as carrier gas, an outlet tube leading to a second polyethylene flask containing NaOH solution (10%), followed by a drying tube and a trap cooled in Dry Ice/MeOH.

An excess of anhydrous hydrogen fluoride was added to the chlorinated ether and the mixture stirred with a magnetic stirrer. Heat was not applied, the temperature remaining at about 20° C. More hydrogen fluoride was added to the mixture as needed until all the organic material had reacted. The weight of material collected from the cold trap was 9.5 g.

Analysis of the recovered product by GC showed it to consist of 84.3% $CF_2HOCF_2Cl$, a yield of 78% based on the $CF_2OCCl_3$ content of the chlorinated mixture. A small amount of $CF_2HOCFCl_2$ was also present.

EXAMPLE 4

Molecular sieves (114 g) were heated to about 250° C. and pumped under vacuum for five hours then placed in a polyethylene tube (17'×⅜"). Impure bis(difluoromethyl)ether prepared as detailed above was then passed through the tube at ambient temperature, and the resulting purified material was collected in a cold trap. The collected material was then transferred to a cylinder for gas chromatograph analysis. The data are shown in Table 2.

TABLE 1

| Run No. | Flow Rates | | | Product Weight (gms) | Product Distribution | | | Moles | | Mole Ratio $Cl_2$/E-152a | Air in Total Gas Flow (%) | Air in Chlorine (%) |
|---|---|---|---|---|---|---|---|---|---|---|---|---|
| | $Cl_2$ | E-152a (mls/min) | Air | | Mono (%) | Di- (%) | Tri- (%) | $Cl_2$ | E152a | | | |
| 6-29-1 | 500 | 273 | — | 69.6 | 6.0 | 42.5 | 33.6 | 0.0203 | 0.0111 | 1.83 | — | — |
| 6-29-2 | 500 | 280 | — | 95.6 | 8.2 | 42.5 | 30.4 | 0.0203 | 0.0114 | 1.78 | — | — |
| 6-29-6 | 510 | 270 | — | 81.4 | 22.5 | 38.5 | 33.7 | 0.0207 | 0.0110 | 1.88 | — | — |
| 6-29-7 | 500 | 280 | — | 79.1 | 23.2 | 42.3 | 37.2 | 0.0203 | 0.0114 | 1.78 | — | — |
| 7-7-3 | 870 | 380 | 67 | 69.3 | 55.0 | 32.9 | 2.8 | 0.0353 | 0.0154 | 2.29 | 5.4 | 7.7 |
| 7-7-4 | 850 | 440 | 65 | 96.8 | 56.8 | 37.0 | 3.5 | 0.0345 | 0.0179 | 1.93 | 5.1 | 7.6 |
| 7-7-5 | 900 | 405 | 63 | 119.3 | 48.3 | 42.4 | 5.2 | 0.0365 | 0.0164 | 2.23 | 4.8 | 7.0 |
| 7-7-7 | 900 | 405 | 60 | 116.0 | 54.3 | 39.8 | 4.5 | 0.0365 | 0.0164 | 2.23 | 4.6 | 6.7 |
| 7-7-8 | 930 | 405 | 62 | 111.5 | 52.5 | 36.2 | 3.3 | 0.0378 | 0.0164 | 2.30 | 4.6 | 6.7 |
| 7-8-2 | 1430 | 600 | 55 | 198.6 | 43.0 | 45.2 | 7.2 | 0.0581 | 0.0244 | 2.38 | 2.7 | 3.8 |
| 7-8-3 | 1850 | 750 | 54 | 202.4 | 42.8 | 46.5 | 5.0 | 0.0751 | 0.0305 | 2.46 | 2.1 | 2.9 |
| 7-8-6 | 2200 | 1030 | 51 | 213.0 | 33.6 | 56.9 | 7.7 | 0.0893 | 0.0418 | 2.14 | 1.6 | 2.3 |

TABLE 2

| Pore Size (Å) | Wt. of $CF_2HOCF_2H$ (g) | Flow Rate (g/min.) | Analysis Before $CF_2HOCH_3$ (ppm) | Analysis Before $CH_2FCl$ (ppm) | Analysis After $CF_2HOCH_3$ (ppm) | Analysis After $CH_2FCl$ (ppm) |
| --- | --- | --- | --- | --- | --- | --- |
| 4–5 | 8.0 | 0.038 | 3000 | 2700 | 0 | 2700 |
| 3 | 15.0 | 0.083 | 3000 | 2700 | 0 | 5700 |
| 3 | 20.0 | 0.083 | 3000 | 2700 | 0 | 4800 |
| 3 | 10.0 | 0.083 | 3000 | 2700 | 90 | 4800 |
| 3 | 35.0 | 0.097 | 1700 | 400 | 0 | 0 |
| 3 | 38.0 | 0.092 | 3000 | 2700 | 0 | 3700 |
| 3 | 35.0 | 0.083 | 3000 | 2700 | 0 | 5000 |

The data show that difluoromethyl methyl ether can be readily removed in the fixed bed process. The increases in $CH_2FCl$ after treatment with molecular sieves is due to inaccuracies in the analytical procedure at the parts per million level.

EXAMPLE 5

Molecular sieves, ranging in size from 3 Å to 10 Å, were heated for about 20 hours to about 250° C. prior to their being used. A weighed amount of a particular size molecular sieve was then placed in a cylinder which was then fitted with a valve and evacuated. A measured amount of bis(difluoromethyl)ether was then added to the cylinder which was then allowed to stand for several allows at ambient temperature. The bis(difluoromethyl)ether was then transferred to another cylinder for GC analysis. The data are shown in Table 3.

TABLE 3

| Pore Size (Å) | Sieves Preheated | Sieve Wt. (g) | $CF_2HOCF_2H$ Wt. (g) | Analysis Before $CH_2FCl$ (ppm) | Analysis Before $CF_2HOCH_3$ (ppm) | Analysis After $CH_2FCl$ (ppm) | Analysis After $CF_2HOCH_3$ (ppm) |
| --- | --- | --- | --- | --- | --- | --- | --- |
| 3 | no | 5.0 | 24.2 | 2000 | 16000 | 2000 | 2000 |
| 3 | yes | 15.0 | 27.0 | 2200 | 4400 | 1500 | 0 |
| 4 | no | 10.0 | 21.3 | 2000 | 16000 | 2000 | 3000 |
| 4 | yes | 10.0 | 17.4 | 400 | 1700 | 40 | 20 |
| 5 | yes | 10.0 | 25.6 | 2700 | 16000 | 600 | 0 |
| 10 | no | 15.2 | 27.6 | 2000 | 3000 | 1300 | 2200 |
| 10 | yes | 10.0 | 27.0 | 1500 | 0 | 900 | 0 |

These data show that in a static system, the molecular sieves have to be heated and pumped before use in order for adsorption to be most effective. Difluoromethyl methyl ether was removed completely by all of the different size molecular sieves tested, provided they were preheated and pumped. Chlorofluoromethane content was reduced substantially, to as low as 40 ppm by the 4 Å sieve.

What is claimed is:

1. A process for the purification of bis(difluoromethyl)ether from impurities comprising difluoromethyl methyl ether and chlorofluoromethane, comprising causing said bis(difluoromethyl)ether and said impurities to contact molecular sieves ranging in pore size from about 3 to about 10 Å, and recovering the resulting purified bis(difluoromethyl)ether.

2. The process of claim 1 further comprising heating said molecular sieves to about 250° C. prior to said contact with bis(difluoromethyl)ether and said impurities.

3. The process of claim 1 further comprising pumping said molecular sieves under vacuum prior to said contact with bis-(difluoromethyl)ether and said impurities.

4. The process of claim 1, wherein said molecular sieves have an average pore size of 4 Å.

5. The process of claim 1, wherein said molecular sieves are contacted with a continuous flow of said bis(difluoromethyl)ether and said impurities.

6. A process for the preparation of fluorinated dimethyl ethers of the formula $CF_2HOCCl_xF_yH_{3-(x+y)}$, wherein x is 0, 1 or 2 and y is 1, 2 or 3 and wherein the total of x+y is 1, 2, or 3, said process comprising:

chlorinating $CHF_2OCH_3$ by reacting said $CHF_2OCH_3$ with chlorine in the presence of oxygen to form a chlorinated admixture containing at least one compound of the formula $CF_2HOCH_{3-z}Cl_z$, wherein z is 1 or 2;

fluorinating said at least one compound of the formula $CF_2HOCH_{3-z}Cl_z$ with a fluorine source selected from the group consisting of hydrogen fluoride, anhydrous hydrogen fluoride, metal salts of $HF_2^{\ominus}$, NaF in the presence of a solvent, KF in the presence of a solvent, and pyridine salts of HF, in the absence of a catalyst to obtain a fluorinated admixture containing at least one compound of formula $CF_2HOCH_{3-z}F_yCl_{z-y}$; and purifying the resulting product from impurities comprising difluoromethyl methyl ether and chlorofluoromethane by contacting it with molecular sieves ranging in pore size from about 3 Å to about 10 Å.

7. The process of claim 6, further comprising inhibiting the formation of $CF_2HOCCl_3$.

8. The process of claim 6, wherein said molecular sieves are contacted with a continuous flow of said resulting product and said impurities.

* * * * *

UNITED STATES PATENT AND TRADEMARK OFFICE
CERTIFICATE OF CORRECTION

PATENT NO. : 5,543,055
DATED : August 6, 1996
INVENTOR(S) : O'Neill et al.

It is certified that error appears in the above-identified patent and that said Letters Patent is hereby corrected as shown below:

On the title page, and in column 1, lines 1-2
<u>In the Title:</u>

"PURIFICATIONS OF FLOURINATED DIMETHYL ETHERS" should read

--PURIFICATION OF FLUORINATED DIMETHYL ETHERS--

Column 1, line 67 "seduce" should read --reduce--

Signed and Sealed this

Thirty-first Day of August, 1999

Attest:

Q. TODD DICKINSON

*Attesting Officer*     *Acting Commissioner of Patents and Trademarks*